United States Patent [19]

Benfatto

[11] Patent Number: 5,575,990
[45] Date of Patent: Nov. 19, 1996

[54] ANTIPERSPIRANT ROLL-ON COMPOSITIONS

[75] Inventor: Anthony Benfatto, North Brunswick, N.J.

[73] Assignee: Bristol-Myers Squibb Company, New York, N.Y.

[21] Appl. No.: 383,396

[22] Filed: Feb. 3, 1995

Related U.S. Application Data

[63] Continuation-in-part of Ser. No. 144,777, Oct. 28, 1993.

[51] Int. Cl.⁶ ......................................... A61K 7/32
[52] U.S. Cl. ..................... 424/65; 252/309; 252/311; 252/312; 424/66; 424/68
[58] Field of Search ................... 424/68, 65, 66; 252/309, 312, 311

[56] References Cited

U.S. PATENT DOCUMENTS

| | | | |
|---|---|---|---|
| 4,264,586 | 4/1981 | Callingham | 424/68 |
| 4,499,069 | 2/1985 | Krafton | 424/66 |
| 4,788,001 | 11/1988 | Narula | 252/312 |
| 4,937,069 | 6/1990 | Shin | 424/66 |
| 5,017,305 | 5/1991 | Hoeffkes et al. | 252/311 |
| 5,069,897 | 12/1991 | Orr | 424/66 |
| 5,098,694 | 3/1992 | Komp et al. | 514/938 |
| 5,098,698 | 3/1992 | Kawam et al. | 424/66 |
| 5,118,497 | 6/1992 | Katsoulis | 514/938 |
| 5,133,897 | 7/1992 | Balzer | 252/312 |
| 5,162,378 | 11/1992 | Guthauser | 514/785 |
| 5,194,262 | 3/1993 | Goldberg et al. | 424/401 |
| 5,213,799 | 5/1993 | Goring et al. | 514/938 |
| 5,225,188 | 7/1993 | Arbutyn | 424/66 |
| 5,268,126 | 12/1993 | Balzer | 252/312 |

FOREIGN PATENT DOCUMENTS

| | | | |
|---|---|---|---|
| 4033928 | 4/1992 | Germany | 252/312 |
| 4301820 | 7/1994 | Germany | 252/312 |
| 2155337 | 9/1985 | United Kingdom . | |
| 9307249 | 4/1993 | WIPO . | |

*Primary Examiner*—Shelley A. Dodson
*Attorney, Agent, or Firm*—Charles J. Zeller

[57] ABSTRACT

The present invention provides for roll-on antiperspirant compositions and more particularly concerns antiperspirant compositions which are clear and, when applied to the human skin, do not leave a visible white residue after drying. The present invention is also particularly concerned with the preparation of clear antiperspirant roll-on compositions which are stable under varying temperature conditions and also provide a suitable cosmetically acceptable feel or sensation when applied to the human skin.

15 Claims, No Drawings

ANTIPERSPIRANT ROLL-ON COMPOSITIONS

This application is a continuation-in-part of U.S. Ser. No. 08/144,777 filed Oct. 28, 1993.

FIELD OF THE INVENTION

The present invention relates to the field of roll-on antiperspirant compositions and more particularly concerns antiperspirant compositions which are clear and, when applied to the human skin, do not leave a white residue after drying. The present invention is also particularly concerned with the preparation of clear antiperspirant roll-on compositions which are stable under varying temperature conditions and also provide a suitable cosmetically acceptable feel or sensation when applied to the human skin.

Specifically, the present invention is directed to clear oil-in-water microemulsion based compositions containing an antiperspirant active component. In a preferred embodiment of the present invention, an antiperspirant composition comprising a particular class of organic nonresinous thickening agents in combination with the aforesaid basic ingredients is taught, which, when admixed, serve to provide a unique composition having a particularly advantageous combination of characteristics when applied to the human skin. In the disclosure which follows, CTFA designated names are those which appear in the CTFA, International Cosmetic Ingredient Dictionary (5th Edition, 1993).

BACKGROUND OF THE INVENTION

The preparation of oil-in-water emulsion based compositions is generally known to the art, but not in the context of their use in preparing a clear low residue antiperspirant composition.

Over the years various workers in the field have attempted to create enhanced antiperspirant emulsion compositions using a variety of ingredients in various combinations all of which have been found to be limited in one respect or another. Amongst the prior art references relating to this area of which the applicant is aware, are the following:

U.S. Pat. No. 4,788,001 to Narula discloses oil-in-water emulsion based compositions as containing an oil, water, and a nonionic three-component emulsifying system, each nonionic surfactant being present in stated concentrations and having a specific HLB requirement. While antiperspirant compositions are not specifically taught by this reference, Narula suggests that the oil-in-water emulsions taught there may find utility in antiperspirant compositions.

U.S. Pat. No. 4,264,586, which issued to Callingham discloses an antiperspirant emulsion composition containing an antiperspirant active, a wax, polydimethyloiloxane, water and an emulsifier.

Witco Tech. Bull. Formula 101A is directed to a clear microemulsion antiperspirant composition containing a mixture of various nonionic surfactants. The composition has a viscosity of 500–5000 cps, and is stable at elevated temperatures.

U.S. Pat. No. 4,499,069 to Krafton is directed to a specific emulsifier system containing PEG (21) stearyl ether.

The foregoing prior art references do not teach or even suggest the totality of the composition of the present invention, nor its equivalents. Further, the known prior art lacks any specific teaching as to the benefits to be achieved by utilizing the particular combination of basic ingredients taught by the applicant herein in order to achieve a clear low residue antiperspirant composition.

SUMMARY OF THE INVENTION

The present invention is directed to roll-on antiperspirant compositions and more particularly to antiperspirant compositions which are clear and which do not leave a visible white residue after drying, when applied to the human skin. In the preferred embodiment, the present invention is particularly concerned with the preparation of clear low residue forming antiperspirant roll-on compositions which are stable under varying temperature conditions and which also provide a suitable cosmetically acceptable feel or sensation when applied to the human skin.

More particularly, the present invention is directed to clear oil-in-water microemulsion based compositions containing an antiperspirant active component. In one preferred embodiment of the present invention, an antiperspirant composition comprising a particular class of organic nonresinous thickening agents in combination with the aforesaid basic ingredients provides a unique composition having a particularly advantageous combination of desirable characteristics, when applied to the skin.

Generally speaking, the clear oil-in-water emulsion compositions which are the subject of the present invention are characterized by the following combination of components:

(a) from about 5 to about 30 wt. % antiperspirant active;

(b) from about 35 to about 60 wt. % water;

(c) from about 5 to about 25 wt. % PEG-7 glyceryl cocoate;

(d) from about 0.5 to about 3 wt % of an emollient, preferably isopropyl myristate;

(e) from about 3 to about 7 wt. % cyclomethicone, and (f) from about 0 to about 3 wt. % of an alkyl polyglucose having from about 6 to 16 carbons, preferably 8 to 12 carbons, in the alkyl group, and an average degree of polymerization of from above about 1 to about 5, preferably about 1.1 to about 2 glucose units, the alkyl polyglucose preferably being present in an amount of from about 0.1 to about 3 wt. % and especially in an amount of from about 0.5 to about 2 wt %, all percentages being by weight of the total composition.

The preferred compositions of the present invention may he generally characterized by the following combination of components:

(a) from about 12 to about 30 wt. % antiperspirant active;

(b) from about 35 to about 50 wt. % water;

(c) from about 15 to about 20 wt. % PEG-7glyceryl cocoate;

(d) from about 0.5 to about 3 wt. % of an emollient, preferably isopropyl myristate;

(e) from about 3 to about 7 wt. % cyclomethicone;

(f) from about 0.1 to about 3 wt. % of an alkyl polyglucose having from about 6 to 16 carbons, preferably 8 to 12 carbons, in the alkyl group, and an average degree of polymerization of from above about 1 to about 5, preferably about 1.1 to about 2 glucose units;

(g) an organic nonresinous thickener such as PEG-150 pentaerythrityl tetrastearate in an amount sufficient to provide a composition viscosity of from about 500 to about 5000 cps, generally from about 0.1 to about 3 wt. %;

(h) an oil-in-water emulsifying system comprising, in a particularly preferred composition:

(i) 0.5–3.0 wt. % Poloxamer 217, (ii) 0.5–3.0 wt. % glycereth-7-benzoate, and (iii) 0–5 wt. % of a nonionic surfactant for high temperature stability, e.g., a water soluble nonoxynol or an octoxynol having from about 7 to about 25, especially 9 to 16, mols of ethylene oxide per molecule or lauric diethanolamide;

(i) 0–0.5 wt. % of a soluble electrolyte as a viscosity control agent and to enhance clarity, preferably sodium chloride;

(j) 0.5–10 wt. % of a humectant for low temperature stability, e.g., a mono- or dialkylene glycol of up to eight carbon atoms, especially dipropylene glycol, and (k) optional ingredients such as buffers, perfumes, fillers, etc., typically each being present in an amount of about 1.0 wt. % or less, all percentages being by weight of the total microemulsion composition.

While various prior art antiperspirant compositions may include some of the components which are also included in the antiperspirant compositions of the present invention, the presence of PEG-7 glyceryl cocoate (Cetiol HE) provides compositions of the present invention that are characteristically clear and leave little or no visible white residue upon drying, after being applied to the human skin.

DETAILED DESCRIPTION OF THE INVENTION

It has been found that the combination of an antiperspirant active ingredient with a particular class of organic nonresinous thickeners and a particular type of oil-in-water emulsifying system together with various other ingredients serves to provide a clear antiperspirant roll-on composition having a particularly advantageous combination of properties, not heretofore available in the art. Unless indicated, all percentages recited in the specification and claims are by weight of the total microemulsion composition.

As used throughout this disclosure, the phrase "nonvisible residue" means that upon drying substantially no residue remains, which might be visible to the human eye.

The desirable objective of producing a clear antiperspirant composition which does not leave a visible residue after drying when applied to the human skin and has a suitable cosmetically acceptable feel to the user while at the same time providing a stable composition under diverse temperature conditions is achieved by preparing a mixture of:

(a) from about 5 to about 30 wt. % antiperspirant active;

(b) from about 35 to about 60 wt. % water;

(c) from about 5 to about 25 wt. % PEG-7-glyceryl cocoate;

(d) from about 0.5 to about 3 wt. % of an emollient, preferably isopropyl myristate;

(e) from about 3 to about 7 wt. % cyclomethicone, and (f) from about 0 to about 3 wt. % of an alkyl polyglucose having from about 6 to 16 carbons, preferably 8 to 12 carbons, in the alkyl group, and an average degree of polymerization of from above about 1 to about 5, preferably about 1.1 to about 2 glucose units.

In addition to the foregoing components, one may also add a number of other ingredients in order to improve the overall qualities of shelf-life, stability and cosmetic feel, in formulating the specific antiperspirant compositions of the preferred embodiments.

Additional ingredients may also be added to provide fragrance or to impart other cosmetic effects to the resultant antiperspirant compositions as will be apparent to one skilled in this art.

The preferred antiperspirant compositions of the present invention are prepared by blending the following combination of components:

(a) from about 12 to about 30 wt. % antiperspirant active;

(b) from about 35 to about 50 wt. % water;

(c) from about 15 to about 20 wt. % PEG-7 glyceryl cocoate;

(d) from about 0.5 to about 3 wt. % of an emollient, preferably isopropyl myristate;

(e) from about 3 to about 7 wt. % cyclomethicone;

(f) an organic nonresinous thickener, such as PEG-150 pentaerythrityl tetrastearate, in an amount to provide a composition viscosity of from about 500 to about 5000 cps, generally from about 0.1 to about 3%;

(g) from about 0.1 to about 3 wt. % of an alkyl polyglucose having from about 6 to 16 carbons, preferably 8 to 12 carbons, in the alkyl group, and an average degree of polymerization of from above about 1 to about 5, preferably about 1.1 to about 2 glucose units;

(h) an oil-in-water emulsifying system, comprising, in a particularly preferred composition:

(i) 0.5–2.0 wt. % Poloxomer 217, (ii) 0.5–2.0 wt. % glycereth-7-benzoate, and (iii) less than 5 wt. % of a nonionic surfactant for high temperature stability, e.g., a water soluble nonoxynol or octoxynol having from about 7 to about 25, especially 9 to 16, mols ethylene oxide per molecule or lauric diethanolamide;

(i) 0–0.5 wt. % of a soluble electrolyte as a viscosity control agent and to enhance clarity, preferably sodium chloride;

(j) a humectant for low temperature stability, e.g., a mono- or dialkylene glycols of up to eight carbon atoms, especially dipropylene glycol, generally in an amount of from about 0.5 to about 10 wt. %, and (k) optional ingredients such as buffers, perfumes, fillers, etc., typically each in an amount of from about 0.01 to about 1.0 wt. %.

The antiperspirant compositions which are the subject of the present invention comprise an antiperspirant active ingredient which may be any one of a number of known and currently commercially available antiperspirant salts. The antiperspirant active will preferably be selected from aluminum zirconium salts or aluminum chlorohydrates. Most preferably the antiperspirant active ingredient used in the compositions of the present invention will be either aluminum zirconium tetrachlorohydrex Gly or aluminum chlorohydrate. The aforesaid preferred antiperspirant active ingredients are both commercially available from industry known chemical suppliers and are generally sold in 35% and 50% solutions in water. It has been found that the antiperspirant active ingredients may be effectively employed in the compositions of the present invention in amounts from about 5% to about 30% by weight of the active ingredient, preferably 12 to 24% by weight.

In formulating the overall antiperspirant composition, water will be present in the overall amount of from about 35% to about 60% by weight, including the amount of water which is added with the antiperspirant active salt solution as well as the additional deionized water which is added in order to make up the final antiperspirant microemulsion.

PEG-7-glyceryl cocoate is a commercially available product produced by Henkel and available under the trade name Cetiol HE. This material is a clear, low viscosity ingredient which, according to the manufacturer, is a self-emulsifying oil suitable for blending with most fatty raw ingredients. Cetiol HE has been recommended by its manufacturer Henkel for use where emolliency is required in aqueous formulations such as shampoos and bubble baths where it has been found to improve skin softness and feel.

While no other commercially available ingredient comparable to Cetiol HE has been identified, it is nonetheless anticipated that other chemically similar components which might exhibit the same chemical characteristics as Cetiol HE will also be appropriate substitutions for PEG-7 glyceryl cocoate in preparing the clear antiperspirant compositions of the present invention.

PEG-7-glyceryl cocoate has been found to be effective in preparing the compositions of the present invention in amounts of from about 5% by weight to about 25% by weight. Preferably this component will be employed in amounts of from about 15 wt. % to about 20 wt. %, most preferably 15 to about 18 wt. %, based upon the total weight of the antiperspirant microemulsion produced.

The clear antiperspirant microemulsion of the present invention also contains an organic liquid emollient material. Suitable emollient materials for use in the microemulsion antiperspirant roll-on composition of the present invention are characterized as being liquid at room temperature and having a viscosity of from about 2 to about 2000 cps, especially from about 10 to about 500 cps at 25° C. Of the suitable emollients, mention may be made of esters of fatty acids having from about 12 to 22, preferably from 14 to 18 carbons in the acid moiety and up to about 6, preferably 3 to 4 carbons in the alcohol residue. Particularly suitable emollients of this type are isopropyl myristate, isopropyl palmitate, isopropyl stearate, ethyl myristate, and the like. Especially preferred is isopropyl myristate. Mention may also be made of branched chain liquid hydrocarbons having 16–40 carbons, especially 20 to 30 carbons in the chain. Hydrogenated polyisobutene is illustrative of this class of hydrocarbon emollients. Low molecular weight alpha olefins are also suitable. Emollients useful in products for application to the skin are identified in CTFA Cosmetic Ingredient Handbook, pp. 79–81 (1st Edition, 1988). Of the enumerated emollients, those having the characteristic properties identified above generally would be expected to behave in a manner consistent with the instant invention. The usefulness of any particular emollient in combination with other constituents is easily measured by simple experiments as set forth in the examples that form a part of this disclosure. Useful emollients are also identified in Balsam & Sagarin, *Cosmetics: Science and Technology*, pp. 27–104 (2nd Ed. 1972).

It has been found that the emollient component, preferably isopropyl myristate, may be effectively employed in the compositions of the present invention in amounts of from about 0.5 to about 3 wt. %. Preferably this component will be employed in amounts of about 2 wt. % based upon the total weight of the resultant microemulsion produced.

Cyclomethicone is a cyclic dimethyl polysiloxane compound that is well known to the art and available from a number of commercial sources. Cyclomethicone is effectively employed in amounts of from about 3 to about 7 wt. % and preferably will be employed in amount of about 5 wt. % based upon the total weight of the final microemulsion produced.

In the preferred embodiment, the roll-on antiperspirant composition will contain from about 0.1 to about 3 wt. % by weight of an alkyl polyglucose (e.g., alkyl glycoside) having 6 to 16 carbons in the alkyl group and above about 1 to about 5 glucose units per molecule, preferably 8 to 12 carbons in the alkyl group and about 1.1 to 2 glucose units per molecule. It has been found that the alkyl polyglucose material improves solubility of the PEG-7-glycereth cocoate in the formulation, particularly at elevated temperatures. Preferably, the alkyl polyglucose is present in an amount of from 0.1 to 2% by weight of the composition. Suitable alkyl polyglucose materials are those made under the Plantaren trade name by Henkel, particularly Plantaren 1200® and Plantaren 2000®. Plantaren 2000® is preferred. See, e.g., Henkel, Tech. Bull, *Plantaren: A New Generation of Surfactants* (1992) and Siracusa, *Alkyl Polyglycosides: A New Category of Surfactants*, HAPPI, p. 100–108 (April 1992), both of which are incorporated herein by reference thereto.

In the preferred embodiments of the present invention in order to produce a clear antiperspirant microemulsion having enhanced feel and other cosmetic attributes, it has been found that a number of additional components may be effectively employed. In particular, it has been found that the use of an organic nonresinous thickener in order to provide a resultant antiperspirant microemulsion composition having a viscosity of from about 500 to about 5000 cps is highly desirable.

In carrying out the preparation of the preferred embodiments of the present invention, the organic nonresinous thickener employed is preferably PEG-150 pentaerythrityl tetrastearate, which is a commercially available material known to those skilled in the art.

Generally speaking from about 0.1 to about 3 wt. % of organic nonresinous thickeners such as the PEG-150 pentaerythrityl tetrastearate may be effectively employed in preparing the clear antiperspirant compositions in accordance with the present invention. Preferably from about 1.5 to about 2.0 wt. % of PEG-150 pentaerythrityl tetrastearate will be employed in producing the preferred clear antiperspirant microemulsion compositions of the present invention.

To further enhance the overall feel and cosmetic appeal of the antiperspirant compositions of the present invention, it has been found that the addition of an oil-in-water emulsifying system comprising a polymeric ether in combination with glycereth-7-benzoate and a nonionic surfactant to provide high temperature stability may be effectively employed.

The polymeric ether is typically a polyoxyethylene/polyoxypropylene or a polyoxypropylene/polyoxyethylene block copolymer. Illustrative are Meroxapols of the generic structure $(PO)_a(EO)_b(PO)_a$ and Poloxamers of the generic structure $(EO)_x(PO)_y(EO)_x$ where EO and PO, respectively, represent ethylene and propylene oxide units and wherein the x, y, a and b values are adjusted to provide an HLB for the material of from about 15 to about 40, preferably 20 to 30. Typically, y has a value of from 30 to 54, especially about 35, and b has a value of about 23 to 39, especially about 34. Illustrative Poloxamers are Poloxamers 185, 188, 217, 237 and 335. An illustrative Meroxapol is Meroxapol 254. Poloxamer 217 is preferred, and is available form a variety of suppliers.

Generally, the polymeric ether emulsifier component of the oil-in-water emulsifying system which is preferably used in preparing the preferred embodiments of the present invention will be present in amounts from about 0.1 to about 2.0 wt. % and will preferably be present in amounts of about 0.5 to about 1.5 wt. % based upon the total weight of the resultant clear antiperspirant microemulsion product.

The glycereth-7-benzoate component of the oil-in-water emulsifying system is a known ingredient which is commercially available and is the benzoated derivative of a polyethylene glycol ether of glycerin.

Generally speaking, from about 0.1 to 2% by weight of the glycereth-7-benzoate component of the oil-in-water emulsifying system has been found to be effective in producing a satisfactory resultant clear antiperspirant microemulsion. Preferably about 0.5 to 1.5 wt. % of glycereth-7-benzoate will be employed.

The nonionic surfactant component of the oil-in-water emulsifying system will generally be present in amounts less than 5 wt. %. Suitable nonionic surfactants are ethoxylated alkyl phenols having an alkyl of 8 or 9 carbons and a degree of ethoxylation of about 7 to about 30, preferably about 9 to about 16 in the case of ethoxylated octyl phenols, and about 10 to about 30 in the case of the ethoxylated nonyl phenols, preferably about 13 to about 18. Other water-soluble nonionic surfactants having an HLB of between about 13 to about 18 may easily be tested as to suitability within the compositions of the present invention. Lauric diethanolamide is also suitable. The preferred materials are known commercially available materials as will be recognized by those skilled in the art. Preferably, the nonionic surfactant will be present in an amount of from about 0.1 to about 2 wt. % based upon the total weight of the resulting clear antiperspirant microemulsion produced. Octoxynol-9 and Octoxynol-16 are preferred.

The soluble electrolyte component which may be added to further control the viscosity and to enhance clarity will preferably be sodium chloride.

It has been found that from about 0.01 to about 0.5 wt. % of soluble electrolyte may be effectively employed. When the soluble electrolyte is the preferred sodium chloride it has been found that from about 0.10 to about 0.13 wt. % may be preferably used in order to provide the degree of viscosity control and clarity enhancement sought.

It has also been found that the use of a humectant to enhance low temperature stability such as for instance a mono- or dialkylene glycol of up to eight carbon atoms, which will preferably be dipropylene glycol, may be effectively employed in producing the preferred clear antiperspirant microemulsion of the present invention. Propylene glycol and 1,3-butylene glycol are also suitable.

Generally speaking, the mono- or dialkylene glycol component may be effectively employed in amounts of from about 0.5 to about 10 wt. % and will preferably be present in amount of about 7 to about 9 wt. % and most preferably in amounts of about 8 wt. % based upon the total weight of the resultant clear antiperspirant microemulsion product.

Various optional ingredients such as buffers, perfumes, fillers and the like may also be added to the clear antiperspirant microemulsion compositions of the present invention as will be understood by those skilled in the art. Typically where such ingredients are utilized they will be each present in amounts of from about 0.05 to about 1.0 wt. % based upon the total weight of the resultant clear antiperspirant microemulsion composition produced, to provide their art recognized function. Preferably where a perfume component is utilized, about 0.5 wt. % will be employed. Glycine, an aminic buffer, may be included in an amount effective to reduce antiperspirant salt irritation, typically less than about 2% by weight.

The oil-in-water microemulsion composition of the present invention comprises an aqueous continuous phase comprising water and the antiperspirant active and a dispersed oil phase comprising the volatile silicone, the emollient, the PEG-7-glyceryl cocoate or its equivalent, and if present the nonresinous thickener. The general procedure is set forth in greater detail in the Examples section of the specification. The emulsifying system is employed to effect distribution of the oil phase within the continuous aqueous phase. Microemulsions are well known in the cosmetics art, and are characterized by disperse phase droplets having a sufficiently small diameter such that the composition as a whole is translucent to light, and perferably is substantially transparent. Generally, the droplets or particles have a diameter of less than about 10 microns, preferably less than about 2 microns, and especially in the submicron range.

The foregoing more general discussion of the present invention will be further illustrated by the following specific examples.

EXAMPLES

GENERAL

Unless otherwise indicated in a specific example the antiperspirant compositions were prepared using the following general procedure, which is inclusive of all components which may be utilized. For those formulations where less than all of the components are employed, the following procedure was suitably modified to eliminate that component, or components, of the formulation not called for.

GENERAL PROCEDURE

Preparation of Water Phase

1. In a suitable vessel, equipped with a homo-mixer, add the formula weight of antiperspirant active in solution, dipropylene glycol, deionized water and sodium chloride. Heat the solution with mixing to 110° F.–120° F.

Preparation of Oil Phase

2. In a separate steam jacket vessel add Cetiol HE, isopropyl myristate, octoxynol-9 and glycereth-7-benzoate, and begin to heat with suitable mixing to 140° F.–145° F.

3. To step (2) add PEG-150 pentaerythritol tetrastearate with continued mixing.

4. To step (3) add Poloxamer 217 with continued mixing.

5. To step (4) add cyclomethicone D-5 with continued mixing.

6. Mix until homogeneous maintaining temperature between 140° F.–145° F.

Preparation of Combined Phases

7. Transfer the oil phase to the water phase with homo-mixing.

8. Continue homogenization and cool the batch to 70°–72° F.

9. To step (8), add perfume with mixing until homogeneous.

10. Take the viscosity at 70°–72° F. If the viscosity is within 1,000±200 cps q.s. with water to 100%. If not proceed to step (11).

ii. Adjust the viscosity by adding melted PEG-150 pentaerythritol tetrastearate (Crothix) and sodium chloride in increments of 0.17 wt. % and 0.03 wt. % respectively with mixing until the viscosity is within specification or the maximum level of Crothix and sodium chloride is reached.

EXAMPLE I

A composition in accordance with the present invention was prepared by admixing the following ingredients in accordance with the general procedure given above, in the proportions indicated.

| Ingredient | Parts By Weight |
|---|---|
| Aluminum Zirconium Tetrachlorohydrex Gly, 35% (Rezal 36 G Soln.) Reheis | 50.00 |
| PEG-7-glyceryl cocoate (Cetiol HE) Henkel | 18.00 |
| Deionized Water | 10.90 |
| Cyclomethicone D-5 | 5.00 |
| Isopropyl Myristate | 2.00 |

Upon evaluation, the foregoing composition was found to be clear and after application to the human skin to dry without leaving a white residue.

EXAMPLE II

A composition not in accordance with the present invention was prepared by admixing the following ingredients in accordance with the general procedure given above, in the proportions indicated.

| Ingredient | Parts By Weight |
|---|---|
| Aluminum Zirconium Tetrachlorohydrex Gly, 35% (Rezal 36 G Soln.) Reheis | 50.00 |
| Deionized Water | 10.90 |
| Cyclomethicone D-5 | 5.00 |
| Isopropyl Myristate | 2.00 |

Upon evaluation, the foregoing composition was found to separate thereby indicating that the presence of PEG-7-glyceryl cocoate is essential to obtaining a clear composition.

EXAMPLE III

A composition in accordance with the present invention was prepared by admixing the following ingredients in accordance with the general procedure given above, in the proportions indicated.

| Ingredient | By Weight |
|---|---|
| Aluminum Zirconium Tetrachlorohydrex Gly, 35% (Rezal 36 G Soln.) Reheis | 50.00 |
| PEG-7-glyceryl cocoate (Cetiol HE) Henkel | 18.00 |
| Deionized Water | 10.90 |
| Cyclomethicone D-5 | 5.00 |
| Isopropyl Myristate | 2.00 |

Upon evaluation, the foregoing composition was found to be clear, which again is attributed to the presence of the PEG-7-glyceryl cocoate component.

EXAMPLE IV

A composition was prepared by admixing the following ingredients in accordance with the general procedure given above, in the proportions indicated.

| Ingredient | % (W/W) |
|---|---|
| Aluminum Zirconium Tetrachlorohydrex Gly, 35% (Rezal 36 G Soln.) Reheis | 50.00 |
| PEG-7-glyceryl cocoate (Cetiol HE) Henkel | 18.00 |
| Deionized Water | 10.37–10.90 |
| Cyclomethicone D-5 | 5.00 |
| Dipropylene glycol (low odor grade) | 8.00 |
| Isopropyl Myristate | 2.00 |
| Octoxynol-9 (Triton X-100) Union Carbide | 2.00 |
| PEG-150 Pentaerythrityl Tetrastearate (Crothix) Croda | 1.50–2.00 |
| Poloxamer 217 (Pluracare F-77) BASF | 1.00 |
| Glycereth-7-benzoate (Dermol G-76) Alzo | 1.00 |
| Perfume | 0.50 |
| Sodium Chloride | 0.10–0.13 |
| | 100.00 |

Upon evaluation, the foregoing composition was found to be clear and upon drying after application to human skin was found to leave no visible white residue.

In addition, the antiperspirant composition of this example was found to impart a highly acceptable feel which proved to be appealing to the user.

EXAMPLE V

A composition was prepared by admixing the following ingredients in accordance with the general procedure given above, in the proportions indicated.

| Ingredient | % (W/W) |
|---|---|
| Aluminum Zirconium Tetrachlorohydrex Gly, 35% | 50.00 |
| Butylene Glycol | 4.00 |
| PEG-7-Glyceryl Cocoate | 18.00 |
| Decyl Polyglucose (Plantaren 2000) | 1.00 |
| Deionized Water | 9.2 |
| Cyclomethicone D-5 | 5.00 |
| Isopropyl Myristate | 2.00 |
| Octoxynol-16, 65% | 3.00 |
| PEG-150 Pentaerythritol Tetrastearate | 1.50 |
| Poloxamer 217 | 0.50 |
| Glycereth-7-Benzoate | 0.50 |
| Dipropylene Glycol | 4.00 |
| Fragrance | 0.30 |
| | 100.00 |

Upon evaluation the foregoing composition was found to be clear and upon drying after application to human skin was found to leave no visible residue.

While a limited number of preferred embodiments of the present invention have been described and tested above, one skilled in the art will, nevertheless, recognize numerous substitution, modifications and alterations which can be made without departing from the spirit and scope of the invention as limited by the following claims.

I claim:

1. In a low-residue oil-in-water microemulsion roll-on antiperspirant composition comprising an aqueous continuous phase containing from about 5 to about 30% of an antiperspirant active component and from about 35 to about 60% water, and a dispersed oil phase containing from about 5 to about 25% PEG-7-glyceryl cocoate, from about 0.5 to about 3% of a liquid organic emollient material having a viscosity of about 2 to about 2000 cps at 25° C., and from about 3 to about 7% cyclomethicone, the improvement comprising incorporating into the dispersed oil phase of said composition from about 0.1 to about 3% of an alkyl polyglucose having 6 to 16 carbons in the alkyl group and above 1 to about 5 glucose units per molecule, all percentages being based upon the total weight of the improved antiperspirant composition, whereby a clear antiperspirant composition is obtained.

2. The composition of claim 1 wherein the antiperspirant active component is present in an amount of from about 12 to about 30%; water is present in an amount of about 35 to about 50%; and PEG-7-glyceryl cocoate is present in an amount of from about 15% to about 20%.

3. The composition of claim 2 wherein the emollient material is selected from the group consisting of esters of fatty acids having from about 14 to about 18 carbons in the acid moiety and from about 3 to about 4 carbons in the alcohol residue; branched chain liquid hydrocarbons having 16 to 40 carbons, glyceryl esters, and low molecular weight alpha-olefins.

4. The composition of claim 3 further comprising an organic nonresinous thickener present in an amount of from about 0.1 to about 3%.

5. The composition of claim 4 wherein the emollient is a fatty acid ester.

6. The composition of claim 5 wherein the organic nonresinous thickener is PEG-150 pentaerythrityl tetrastearate.

7. The composition of claim 2, 3 or 5 further comprising an oil-in-water emulsifying system of nonionic emulsifiers.

8. The composition of claim 7 wherein the oil-in-water emulsifying system comprises by weight of the total composition from about 0.1 to about 2% polyoxyethylene/ polyoxypropylene block copolymer having an HLB of from about 15 to about 40, from about 0.1 to about 2% glycereth-7-benzoate and less than 5% of a nonionic surfactant.

9. The composition of claim 8 wherein the block copolymer is selected form the group consisting of Poloxamers 185, 188, 217, 237 and 235, and wherein the nonionic surfactant is selected from the group consisting of lauric diethanolamide and ethoxylated octyl and nonyl phenols having an HLB of from about 13 to about 18.

10. The composition of claim 7 which also comprises a soluble electrolyte as a viscosity control agent.

11. The composition of claim 7 further comprising from about 0.5 to about 10% of a humectant to impart low temperature stability.

12. The composition of claim 11 wherein the humectant is a mono- or dialkylene glycol of up to 8 carbon atoms.

13. The composition of claim 11 wherein the alkyl polyglucose is present in the amount of from 0.1 to 2%.

14. The composition of claim 11 wherein the oil-in-water emulsifying system comprises by weight of the total composition from about 0.1 to about 2% polyoxyethylene/ polyoxypropylene block copolymer having an HLB of from about 15 to about 40, from about 0.1 to about 2% glycereth-7-benzoate and less than 5% of a nonionic surfactant.

15. The composition of claim 12 wherein the block copolymer is selected form the group consisting of Poloxamers 185, 188, 217, 237 and 235, and wherein the nonionic surfactant is selected from the group consisting of lauric diethanolamide and ethoxylated octyl and nonyl phenols having an HLB of from about 13 to about 18.

* * * * *